United States Patent [19]

Packer et al.

[11] Patent Number: 4,626,598

[45] Date of Patent: Dec. 2, 1986

[54] PURIFICATION OF TEREPHTHALIC ACID

[75] Inventors: Lawrence G. Packer, Lisle; David E. James, Batavia, both of Ill.

[73] Assignee: Amoco Corporation, Chicago, Ill.

[21] Appl. No.: 745,620

[22] Filed: Jun. 17, 1985

[51] Int. Cl.$^4$ .............................................. C07C 51/42
[52] U.S. Cl. .................................. 562/487; 502/185; 562/485
[58] Field of Search ................ 562/485, 487; 502/185

[56] References Cited

U.S. PATENT DOCUMENTS

| | | | |
|---|---|---|---|
| 3,546,285 | 12/1970 | Witt | 562/487 |
| 3,584,039 | 6/1971 | Meyer | 562/487 X |
| 3,639,465 | 2/1972 | Olsen et al. | 562/487 |
| 3,726,915 | 4/1973 | Pohlmann | 562/487 |
| 4,126,638 | 11/1978 | Alagy et al. | 562/487 |
| 4,405,809 | 9/1983 | Stech et al. | 562/487 |

*Primary Examiner*—Natalie Trousof
*Assistant Examiner*—Vera C. Clarke
*Attorney, Agent, or Firm*—James R. Henes; William T. McClain; William H. Magidson

[57] ABSTRACT

An improved method for producing purified terephthalic acid by catalytic hydrogenation is disclosed. Control of the reduction of colored compounds during the production of purified terephthalic acid is effected by modulating solution hydrogen concentration during hydrogenation.

14 Claims, No Drawings

PURIFICATION OF TEREPHTHALIC ACID

TECHNICAL FIELD

This invention relates to a method for purification of terephthalic acid.

BACKGROUND OF THE INVENTION

Polymer grade terephthalic acid is the starting material for polyethylene terephthalate (PET), which is the principal polymer for polyester fibers, polyester films, and resins for bottles and the like containers. Polyester fibers are used in textiles as well as in industrial applications such as tire cord. Polyester films coated with adhesives and emulsions are useful as wrapping tapes, photographic films, recording tapes, and the like.

Polymer grade terephthalic acid is derived from relatively less pure, technical grade terephthalic acid by purification of the latter utilizing hydrogen and a noble metal catalyst as described in U.S. Pat. No. 3,584,039 to Meyer. In the purification process, the impure terephthalic acid is dissolved in water at an elevated temperature, and the resulting solution hydrogenated, preferably in the presence of a hydrogenation catalyst, e.g., palladium on a carbon support, as described in U.S. Pat. No. 3,726,915 to Pohlmann. This hydrogenation step converts the various color bodies present in the relatively impure terephthalic acid to colorless products. The principal feedstock impurity, 4-carboxybenzaldehyde, is converted to p-toluic acid. Color-forming precursors and color bodies present as impurities are believed to be of the benzil, fluorenone and/or antraquinone type.

The resulting purified product, polymer grade terephthalic acid, is recovered by crystallization, centrifugation, and drying. Another related purification-by-hydrogenation process for aromatic polycarboxylic acids produced by liquid phase catalytic oxidation of polyalkyl aromatic hydrocarbons is described in U.S. Pat. No. 4,405,809 to Stech et al.

However, the variable nature of the impure terephthalic acid feedstock makes process control, and thus quality assurance, difficult and costly. To this end, it would be desirable to effect hydrogenation of an aqueous, impure terephthalic acid solution under conditions that optimize control of the reduction of colored compounds. The present invention provides a convenient method for accomplishing this objective.

SUMMARY OF THE INVENTION

It has now been found that the color of terephthalic acid purified by hydrogenation is inversely proportional to the solution hydrogen concentration in a relatively impure, aqueous terephthalic acid solution which is hydrogenated and from which the purified terephthalic acid has been derived. Thus, the color level of purified terephthalic acid in batch or continuous processes can be controlled effectively by modulating the hydrogen concentration in the impure aqueous solution while it is undergoing hydrogenation. An increase in the solution hydrogen concentration results in a decrease in the color level of the purified terephthalic acid, and vice versa. The modulation is effected in direct or indirect response to the b*-value of the produced terephthalic acid on the Hunter Color Scale by adjusting reactor hydrogen partial pressure and/or hydrogen flow rate into the impure aqueous solution.

In a continuous purification process, solution hydrogen concentration in the hydrogenation reactor can be adjusted directly on the basis of b*-value change in the obtained purified product or indirectly on the basis of a change in optical density of the feed solution to a light beam having a wavelength of 340 nanometers (nm), the b*-value change being a function of the optical density change at 340 nm for given hydrogenation conditions.

Specifically, it has been found that a 0.1-unit change in the b*-value of the obtained product, i.e., terephthalic acid, can be compensated by an adjustment of dissolved hydrogen concentration in the impure terephthalic acid solution in the range of about 0.03 to about 0.3 cubic centimeters/gram (cc/g), depending upon the activity of the particular catalyst that is employed. The volume of dissolved hydrogen is that at 1 atmosphere absolute pressure and 0° C. (32° F.).

Thus, a 0.1-unit change in the b*-value of the obtained product can also be compensated, depending upon the activity of the catalyst employed, by an adjustment in reactor hydrogen partial pressure of as little as about 5 pounds per square inch (psi) to as high as about 60 psi. An increase in reactor hydrogen partial pressure results in a decrease in the product b*-value, and a decrease in reactor hydrogen partial pressure results in an increase in the product b*-value. Also, a 0.1-unit change in feed optical density to light having a wavelength of 340 nanometers (nm) can cause about a 0.05-unit change in the b*-value of the purified terephthalic acid obtained from that feed. Accordingly, a 0.1-unit change in the feed optical density at 340 nm can be compensated as well by an adjustment in reactor hydrogen partial pressure of as little as about 2.5 psi to as high as about 30 psi.

The purified terephthalic acid is useful for direct esterification with a diol, e.g., ethylene glycol, followed by polycondensation to produce relatively high molecular weight polyesters that can be fabricated into fibers, films, sheets, and the like.

DESCRIPTION OF PREFERRED EMBODIMENTS

The process embodying the present invention is conducted at an elevated temperature and pressure with the terephthalic acid to be purified dissolved in water or like polar solvent. Water is the preferred solvent; however, other suitable polar solvents are the relatively lower molecular weight alkyl carboxylic acids, alone or admixed with water.

Reactor, and thus solution, temperatures during purification can be in the range of about 500° F. to about 600° F., preferably about 530° F. to about 550° F., and more preferably about 535° F. to about 545° F.

Reactor pressure conditions primarily depend upon the temperature at which the purification process is carried out. Inasmuch as the temperatures at which practical amounts of the impure terephthalic acid may be dissolved are substantially above the normal boiling point of the polar solvent, the process pressures are necessarily considerably above atmospheric pressure. The reactor pressure can be maintained by gaseous hydrogen alone or in admixture with an inert gas such as water vapor and/or nitrogen. The use of an inert gas in admixture with hydrogen also can provide an advantageous means for modulating the reactor hydrogen partial pressure, especially at relatively low hydrogen partial pressures. To this end, the inert gas is preferably admixed with hydrogen prior to introduction into the reactor. In general, under normal operation, the reactor pressure during hydrogenation can be in the range of about 950 to about 1200 pounds per square inch gauge (psig).

The hydrogenation reactor can be operated in several modes. For example, a predetermined liquid level can be maintained in the reactor and hydrogen can be fed in, for any given reactor pressure, at a rate sufficient to maintain the predetermined liquid level. The difference between the actual reactor pressure and the vapor pressure of the terephthalic acid solution present is the hydrogen partial pressure in the reactor vapor space. Alternatively, if hydrogen is fed in admixture with an inert gas such as nitrogen, the difference between the actual reactor pressure and the vapor pressure of the terephthalic acid solution present is the combined partial pressure of hydrogen and the inert gas admixed therewith. In this case the hydrogen partial pressure can be calculated from the known relative amounts of hydrogen and inert gas present in the admixture.

In yet another operating mode the reactor can be filled with the terephthalic acid solution so as to provide no reactor vapor space. That is, the reactor can be operated as a hydraulically full system with hydrogen being fed to the reactor by flow control. In such an instance, the solution hydrogen concentration can be modulated by adjusting the hydrogen flow rate to the reactor. If desired, a pseudo-hydrogen partial pressure value can be calculated from the solution hydrogen concentration which, in turn, can be correlated with the hydrogen flow rate to the reactor.

In the operating mode where process control is effected by adjusting the hydrogen partial pressure, the hydrogen partial pressure in the reactor preferably is in the range of about 10 psi to about 200 psi, or higher, depending upon the service pressure rating of the reactor, the degree of contamination of the impure terephthalic acid, the activity and age of the particular catalyst employed, and like processing considerations.

In the operating mode where process control is effected by adjusting directly the hydrogen concentration in the feed solution, the latter is less than saturated with respect to hydrogen and the reactor itself is hydraulically full. Thus an adjustment of the hydrogen flow rate to the reactor will result in the desired proportional modulation of hydrogen concentration in the solution.

The amount of hydrogen supplied under reaction conditions usually is in the range of about 1 to about 5 moles in excess over the stoichiometric amount required to reduce the principal reducible impurity, 4-carboxybenzaldehyde, as well as the characteristically yellow-colored impurities that may be present.

Hydrogenation of the impure terephthalic acid solution is effected in the presence of a noble metal catalyst which can be used supported or unsupported. A wide variety of hydrogenation catalysts is available for this purpose. A typical noble metal-bearing catalyst comprises abiout 0.01 to about 1 weight percent of a noble metal, calculated as the elemental metal and based on the total weight of the catalyst, supported on a porous inert support structure such as charcoal. The support structure preferably has a surface area in the range of about 1,000 to about 2,000 square meters per gram. Noble metals particularly well suited as catalysts for the present purposes are platinum and palladium. A particularly preferred catalyst is palladium on carbon.

Other catalysts effective for aqueous phase hydrogenation under the relatively mild hydrogenation conditions described hereinabove are listed in Kirk-Othmer, "*Encyclopedia of Chemical Technology*" (Wiley-Interscience), particularly in the chapters on Hydrogenation and Catalysts. See also U.S. Pat. Nos. 2,070,770 to Amend and 2,105,664 to Lazier. Illustrative other Group VIII noble metals suitable as catalysts for the present purposes are ruthenium, rhodium, osmium, and iridium.

The present purification process can be carried out in a batch mode as well as a continuous mode. For commercial scale purification of terephthalic acid the continuous mode is preferred. In any event, however, the color of the obtained purified terephthalic acid is monitored and the hydrogen partial pressure in the reactor adjusted so as to maintain the desired color level of the purified product.

The color level of the purified product can be monitored or evaluated directly or indirectly, as described hereinbelow. The reactor hydrogen partial pressure is then adjusted to compensate for any detected impermissible deviation from the desired color level.

The color level of the purified product can be ascertained by measuring its b*-value on the Hunter Color Scale as described in Hunter, "*The Measurement of Appearance,*" Chapter 8, pp. 102–132, John Wiley & Sons, N.Y., N.Y. (1975), and in Wyszecki et al., "*Color Science, Concepts and Methods, Quantitative Data and Formulae,*" 2d Ed., pp. 166–168, John Wiley & Sons, N.Y., N.Y. (1982).

More specifically, the b*-value of purified terephthalic acid can be determined using, for example, a Diano Match Scan Spectrophotometer as follows. Purified terephthalic acid is pressed into a pellet having a thickness of about 0.25 inch and a diameter of about 1 inch. The pellet is then irradiated with white light that has been UV-filtered. The spectrum of the visible light reflected from the sample is determined and tristimulus values (X, Y, and Z) are computed using the CIE Standard Observer functions. Using the weighted-ordinate method, tristimulus values are obtained from the following equations:

$$X = \sum_{400}^{700} R_\lambda \bar{x}_\lambda, \quad Y = \sum_{400}^{700} R_\lambda \bar{y}_\lambda, \quad Z = \sum_{400}^{700} R_\lambda \bar{z}_\lambda,$$

where $R_\lambda$ is the percent reflectance of the object at wavelength $\lambda$ and $\bar{x}_\lambda$, $\bar{y}_\lambda$, and $\bar{z}_\lambda$ are the Standard Observer functions at wavelength $\lambda$ for CIE Illuminant D65. The tristimulus values X, Y and Z, identify the color of the object in terms of the mixture of the primary lights that match it visually. Tristimulus values, however, are of limited use as color specifications, because they do not correlate with visually meaningful attributes of color appearance and are not uniform in the spacing of colors as related to visual differences. As a result, "Uniform Color Scales" (UCS) have been adopted which use simple equations to approximate visual response. The UCS scale used by the Diano instrument is the CIE 1976 L*a*b* formula which converts tristimulus values to L*, a*, and b* values as shown below:

$$L^* = 25(100Y/Y_o)^{\frac{1}{3}} - 16$$

$$a^* = 500[(X/X_o)^{\frac{1}{3}} - (Y/Y_o)^{\frac{1}{3}}]$$

$$b^* = 200[(Y/Y_o)^{\frac{1}{3}} - (Z/Z_o)^{\frac{1}{3}}]$$

The L*-value is a measure of the luminosity or whiteness of an object where L*=100 is pure white, L*=0 is black, and in between is gray. The L*-value is strictly a function of the tristimulus Y-value. The b*-value is a measure of the yellowness-blueness attribute where positive b*-values repsent yellow appearance and negative b*-values represent blue appearance. The b*-value is a function of both tristimulus values Y and Z.

Alternatively, by the aforesaid indirect method, the color level, e.g., b*-value, of the purified product can be correlated with the optical density (OD) of the incoming impure terephthalic acid solution feed to the reactor by routine tests and the optical density of the incoming feed utilized to adjust the reactor hydrogen partial pressure. Typically, the optical density values can be determined using a spectrophotometer and a light beam having a wavelength of 340 nanometers (nm) or millimicrons (mu), correlated with the product b*-value at a given hydrogen partial pressure for a specific catalyst, and then used to adjust the hydrogen partial pressure during a particular process run so as to produce a purified product having the desired b*-value.

It has been found that a 0.1-unit deviation in the b*-value of a product can be compensated by an adjustment in reactor hydrogen partial pressure of as low as about 5 psi to as high as about 60 psi, depending upon the activity of the catalyst employed. If a fresh, relatively high activity catalyst is utilized, the initial adjustment in hydrogen partial pressure for a 0.1-unit deviation in the b*-value usually is about 5 psi to about 7.5 psi. However, as the catalyst stabilizes, the adjustment in hydrogen partial pressure for a 0.1-unit deviation in the b*-value usually is about 40 psi to about 50 psi.

Similarly, it has been found that a 0.1-unit change in feed solution optical density at 340 nm ($OD_{340}$) causes about a 0.5-unit change in the b*-value of the purified terephthalic acid that is derived from that particular feed solution. Thus, a 0.1-unit change in $OD_{340}$ of the feed solution usually can be initially compensated by an adjustment in reactor hydrogen partial pressure of about 2.5 psi to about 4 psi for a fresh, relatively high activity catalyst. However, as the activity of catalyst stabilizes during use, a 0.1-unit change in $OD_{340}$ of the feed solution usually can be compensated by an adjustment in reactor hydrogen partial pressure of about 20 psi to about 25 psi.

The overall relationship among b*-value, hydrogen partial pressure, and optical density at 340 nm can also be expressed as b*-value $\alpha A(H_2 \text{ pp}) + C(OD_{340})$ wherein $H_2$ pp designates hydrogen partial pressure expressed in psi, $OD_{340}$ is the optical density value of the crude terephthalic acid feed solution, A has a value of about 0.001 to about 0.03, and C has a value of about 0.4 to about 1.4.

Similarly, the overall relationship among b*-value, solution hydrogen concentration, and optical density at 340 nm can be expressed as b*-value $\alpha D(H_2 \text{ conc.}) + C(OD_{340})$ wherein $H_2$ conc. designates solution hydrogen concentration in cubic centimeters of hydrogen at 1 atmosphere absolute pressure and 0° C. (32° F.) dissolved per gram of crude terephthalic acid feed solution, $OD_{340}$ is the optical density value of the crude terephthalic acid feed solution, D has a value of about 0.2 to about 5.75, and C has a value of about 0.4 to about 1.4.

If it is desired to modulate the solution hydrogen concentration in a hydraulically full reactor directly by adjusting the flow of gaseous hydrogen to the hydrogenation reactor, then in such an event the hydrogen flow rate can be adjusted to provide a change in solution hydrogen concentration in the range of about 0.03 cc/g to about 0.3 cc/g for a 0.1-unit change in the product b*-value to be implemented, or in the range of about 0.015 cc/g to about 0.15 cc/g for an observed 0.1-unit change in $OD_{340}$ of the feed solution to the hydrogenation reactor.

The terephthalic acid concentration in the solution to be purified by hydrogenation can vary over a relatively wide range. The concentration can be as low as about 5 percent by weight or as high as about 35 percent by weight, based on the weight of the solution. Preferably the solution concentration of terephthalic acid is in the range of about 10 to about 30 percent by weight.

The present invention is illustrated by the following Examples.

EXAMPLE 1

Modulation of Reactor Hydrogen Partial Pressure to Maintain a Predetermined Product b*-Value Crude terephthalic acid derived by oxidation of p-xylene using a Co/Mn/Br catalyst was fed as an aqueous solution, containing about 30 wt-% of terephthalic acid, to a fixed bed reactor containing a relatively fresh Pd-on-carbon catalyst (about 0.5 wt-% Pd). Gaseous hydrogen was dissolved in the solution under pressure just prior to the time the solution entered the catalyst bed and the hydrogen partial pressure within the reactor was monitored. The optical density of the aqueous feed solution to the reactor was also measured using light at 340 nm wavelength ($OD_{340}$).

The obtained, hydrogenated terephthalic acid solution was cooled sufficiently to precipitate the terephthalic acid present, the obtained precipitate was then separated from the liquid phase present, washed with water, and dried. The b*-value of the dried product was also determined.

The experimental data obtained are presented in tabular form below.

TABLE I

Effect of Feed $OD_{340}$ on b*-Value at Substantially Constant Hydrogen Partial Pressure

| $H_2$pp, psi | $OD_{340}$ | b*-Value |
|---|---|---|
| 113 | 0.9 | 0.7 |
| 111 | 1.2 | 1.2 |
| 112 | 1.3 | 1.4 |

Data in Table 1 demonstrate that at substantially constant reactor hydrogen partial pressure the b*-value of purified terephthalic acid increases as the $OD_{340}$ value of the feed solution to be purified increases.

TABLE II

Effect of Hydrogen Partial Pressure on b*-Value at Constant Feed Optical Density

| $H_2$pp, psi | $OD_{340}$ | b*-Value |
|---|---|---|
| 111 | 1.2 | 1.2 |
| 134 | 1.2 | 0.8 |

Data in Table II demonstrate that for a constant optical density at 340 nm of the feed solution the b*-value of the purified terephthalic acid is decreased with an increasing reactor hydrogen partial pressure.

TABLE III

Maintenance of Constant Product b*-Value by Adjustment of Hydrogen Partial Pressure When Optical Density of Feed Solution Varies

| $H_2$pp, psi | $OD_{340}$ | b*-Value |
|---|---|---|
| 113 | 0.9 | 0.7 |
| 124 | 1.1 | 0.7 |

Data in Table III demonstrate that an adjustment of reactor hydrogen partial pressure can maintain a constant purified product b*-value while the optical density of the feed solution varies.

EXAMPLE 2

Purification of Crude Terephthalic Acid

Crude terephthalic acid derived by oxidation of p-xylene using a Co/Mn/Br catalyst was fed as an aqueous solution, containing about 26 wt-% of terephthalic acid, to a fixed bed reactor containing a Pd-on-carbon catalyst (about 0.5 wt-% Pd). Gaseous hydrogen was fed directly to the reactor and the hydrogen partial pressure within the reactor was monitored. The optical density of the aqueous feed solution to the reactor was also measured using light at 340 nm wavelength.

The obtained, hydrogenated terephthalic acid solution was then cooled sufficiently to precipitate the terephthalic acid present, the obtained precipitate was then separated from the liquid phase present, washed with water, and dried. Thereafter the b*-value of the dried product was determined.

The experimental observations are presented in Table IV, below.

TABLE IV

| Test No. | Reactor Press., psig | $H_2$pp, psi | $OD_{340}$ | b*-Value |
|---|---|---|---|---|
| 1 | 1015 | 113 | 0.83 | 0.82 |
| 2 | 1070 | 168 | 0.92 | 0.71 |
| 3 | 960 | 58 | 0.76 | 0.99 |
| 4 | 1070 | 168 | 0.79 | 0.70 |

EXAMPLE 3

Purification of Crude Terephthalic Acid Using a Relatively Younger Catalyst

In a manner similar to Example 2 a crude terephthalic acid solution in water was fed to a fixed bed reactor containing a Pd-on-carbon catalyst (about 0.5 wt-% Pd) of a relatively lower age than that used for the test runs of Example 2.

The experimental results are compiled in Table V, below.

TABLE V

| Test No. | Reactor Press., psig | $H_2$pp, psi | $OD_{340}$ | b*-Value |
|---|---|---|---|---|
| 5 | 1015 | 113 | 0.71 | 0.92 |
| 6 | 1070 | 168 | 0.74 | 0.76 |
| 7 | 980 | 78 | 0.73 | 1.03 |
| 8 | 1070 | 168 | 0.80 | 0.76 |

EXAMPLE 4

Purification of Crude Terephthalic Acid Using a Hydraulically Full Reactor

Crude terephthalic acid derived by oxidation of p-xylene using a Co/Mn/Br catalyst was fed as an aqueous solution, containing about 31.5 wt-% of terephthalic acid, to a fixed bed reactor containing a Pd-on-carbon catalyst (about 0.5 wt-% Pd). The reactor was kept hydraulically full during the test runs. Hydrogen was admixed with the feed solution prior to entry into the reactor, the hydrogen flow rate was monitored, hydrogen concentration in the feed solution was calculated, and psuedo-hydrogen partial pressure was derived therefrom.

The obtained, hydrogenated terephthalic acid solution was then cooled sufficiently to precipitate the terephthalic acid present, the obtained precipitate was then separated from the liquid phase present, washed with water, and dried. Thereafter the b*-values of the dried product was determined.

The observed experimental results are set forth in Table VI, below.

TABLE VI

| Test No. | $H_2$ Flow Rate, SCFH | $H_2$ Feed Conc'n, cc/g | $H_2$pp, psi[1] | $OD_{340}$ | b*-Value |
|---|---|---|---|---|---|
| 9 | 6000 | 0.71 | 136 | 0.77 | 0.68 |
| 10 | 8000 | 0.94 | 180 | 0.77 | 0.60 |
| 11 | 8000 | 0.94 | 180 | 0.77 | 0.55 |
| 12 | 5000 | 0.59 | 113 | 0.76 | 0.68 |

[1] derived pseudo-hydrogen partial pressure.

The foregoing description of this invention and the accompanying examples are intended as illustrative and are not to be taken as limiting. Still other variations in the process conditions and parameters are possible and will readily present themselves to those skilled in the art.

We claim:

1. In a method for producing purified terephthalic acid by catalytic hydrogenation of a relatively impure terephthalic acid solution in a polar solvent, the improvement which comprises the step of modulating solution hydrogen concentration during said hydrogenation so as to maintain a predetermined color scale b*-value in the purified terephthalic acid.

2. In a continuous process for purifying the catalytic hydrogenation in a reactor a relatively impure, aqueous terephthalic acid solution, the improvement which comprises the steps of
   recovering purified terephthalic acid from a hydrogenated product stream;
   determining the color scale b*-value of the recovered terephthalic acid; and
   adjusting the reactor hydrogen partial pressure to provide terephthalic acid having a predetermined color scale b*-value.

3. The improvement in accordance with claim 2 wherein the hydrogen partial pressure within the reactor is adjusted about 5 psi to about 60 psi for a 0.1-unit change in the color scale b*-value to be implemented.

4. The improvement in accordance with claim 2 wherein terephthalic acid concentration in said relatively impure aqueous solution is about 5 to about 35 percent by weight, based on the weight of the solution.

5. The improvement in accordance with claim 2 wherein terephthalic acid concentration in said relatively impure aqueous solution is about 10 to about 30 percent by weight, based on the weight of the solution.

6. The improvement in accordance with claim 2 wherein the hydrogen partial pressure within the reactor is maintained within the range of about 10 to about 200 pounds per square inch.

7. The improvement in accordance with claim 2 wherein temperature within the reactor during hydrogenation is maintained within the range of about 530° F. to about 550° F.

8. The improvement in accordance with claim 2 wherein temperature within the reactor during hydrogenation is maintained within the range of about 535° F. to about 545° F.

9. In a continuous process for purifying by catalytic hydrogenation in a reactor a relatively impure, aqueous terephthalic acid solution, the improvement which comprises the steps of
   monitoring the optical density of the aqueous terephthalic acid solution to be hydrogenated to a light beam having a wavelength of 340 nanometers; and
   adjusting the reactor hydrogen partial pressure in response to a change in said optical density sufficient to provide purified terephthalic acid having a substantially constant color scale b*-value.

10. The improvement in accordance with claim 9 wherein the hydrogen partial pressure within the reactor is adjusted about 2.5 psi to about 25 psi for a 0.1-unit change in said optical density.

11. In a continuous process for purifying by catalytic hydrogenation in a hydraulically full reactor a relatively impure, aqueous terephthalic acid solution, the improvement which comprises the steps of
   recovering purified terephthalic acid from a hydrogenated product stream;
   determining the color scale b*-value of the recovered terephthalic acid; and
   adjusting gaseous hydrogen flow rate to the reactor to provide terephthalic acid having a predetermined color scale b*-value.

12. The improvement in accordance with claim 11 wherein the hydrogenation flow rate is adjusted to provide a change in solution hydrogen concentration in the range of about 0.03 to 0.3 cubic centimeters at 1 atmosphere (absolute) and 0° C. per gram for a 0.1-unit change in the color scale b*-value to be implemented.

13. In a continuous process for purifying by catalytic hydrogenation in a hydraulically full reactor a relatively impure, aqueous terephthalic acid solution, the improvement which comprises the steps of
   monitoring the optical density of the aqueous terephthalic acid solution to be hydrogenated to a light beam having a wavelength of 340 nanometers; and
   adjusting gaseous hydrogen flow rate to the reactor to provide terephthalic acid having a predetermined color scale b*-value.

14. The improvement in accordance with claim 13 wherein the hydrogen flow rate is adjusted to provide a change in solution hydrogen concentration in the range of about 0.015 to about 0.15 cubic centimeters at 1 atmosphere (absolute) and 0° C. per gram for 0.1-unit change in said optical density.

* * * * *

UNITED STATES PATENT OFFICE
CERTIFICATE OF CORRECTION

Patent No. 4,626,598            Dated   December 2, 1986

Inventor(s)   Lawrence G. Packer & David E. James

It is certified that error appears in the above-identified patent and that said Letters Patent are hereby corrected as shown below:

Column 10, Line 11, "hydrogenation" should be --hydrogen--

Signed and Sealed this

Twenty-first Day of April, 1987

Attest:

DONALD J. QUIGG

Attesting Officer          Commissioner of Patents and Trademarks